United States Patent [19]

Wood

[11] 4,379,412
[45] Apr. 12, 1983

[54] SAMPLING PROBE FOR STACK GAS MONITORING SYSTEM

[75] Inventor: Richard D. Wood, Lewisburg, W. Va.

[73] Assignee: The Bendix Corporation, Southfield, Mich.

[21] Appl. No.: 332,705

[22] Filed: Dec. 21, 1981

[51] Int. Cl.³ .............................................. G01N 1/24
[52] U.S. Cl. ............................... 73/863.24; 73/864.73
[58] Field of Search ........... 73/863.11, 863.21, 863.24, 73/864.34, 864.73

[56] References Cited

U.S. PATENT DOCUMENTS

| | | | |
|---|---|---|---|
| 1,809,325 | 6/1931 | Austin et al. | 73/864.73 |
| 3,070,990 | 1/1963 | Krinov | 73/863.12 |
| 3,289,481 | 12/1966 | Barnes | 73/863.12 |
| 3,759,087 | 9/1973 | Iwao | 73/863.12 |
| 4,161,883 | 7/1979 | Land et al. | 73/421.5 |

*Primary Examiner*—S. Clement Swisher
*Attorney, Agent, or Firm*—Bruce L. Lamb; W. G. Christoforo

[57] ABSTRACT

A tube closed at the end by plugs having axial bores therein and which support a hollow, porous walled cylinder concentrically within the tube to form a conduit interconnecting the plug bores while allowing a clearance space between the cylinder outer wall and the tube inner wall. A combined ejector-blowback valve is secured to one plug externally of the tube for inducing gas flow through the plug bores and cylinder in one valve position and for reversing flow through the plug bores and cylinder in a second valve position to dislodge and discharge adherent material. The probe is mounted with the end opposite the ejector-blowback valve extending into the gas stream to be sampled. Gas samples are withdrawn from the clearance space surrounding the cylinder. The probe is constructed substantially entirely of corrosion and temperature resistant ceramic material.

3 Claims, 4 Drawing Figures

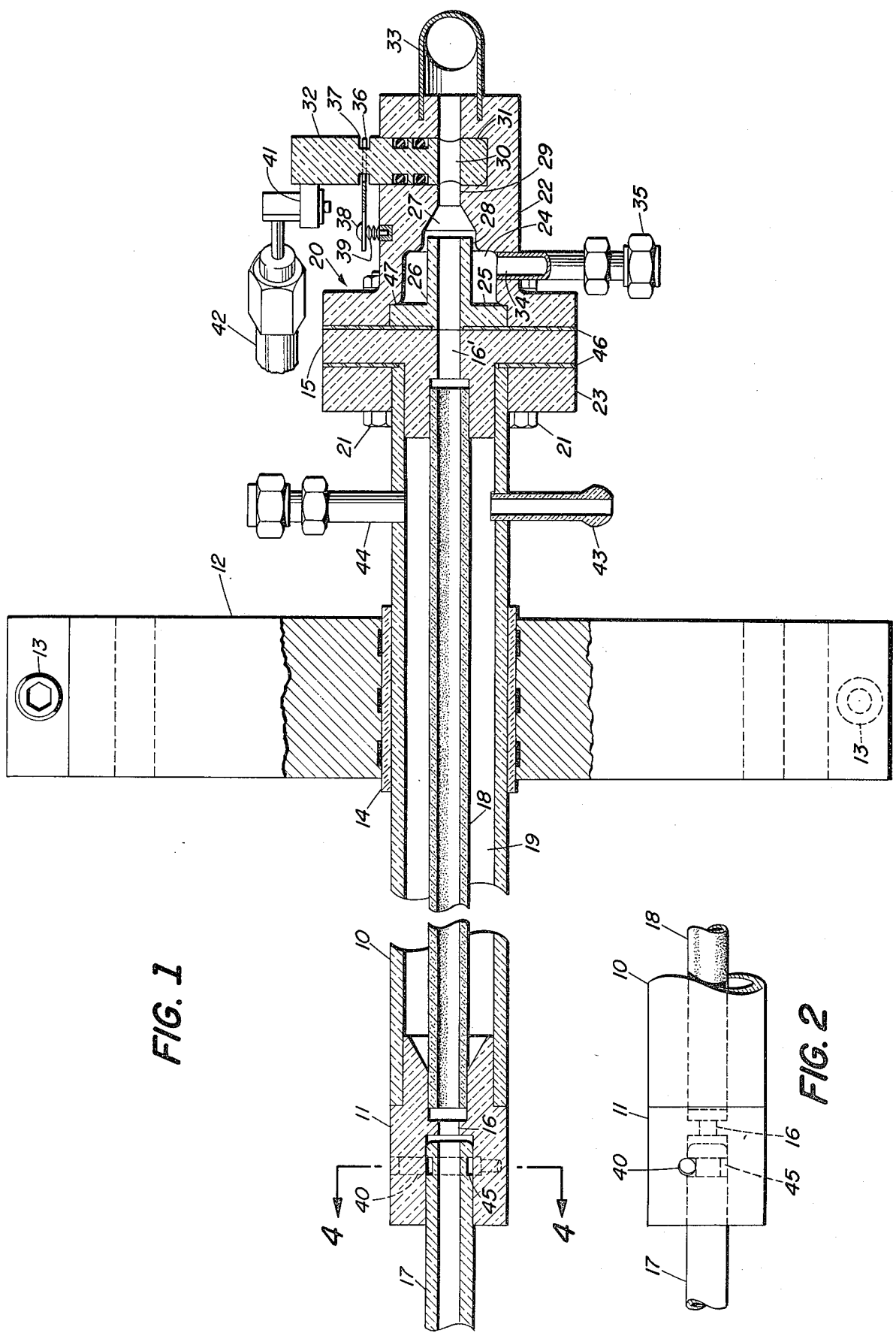

SAMPLING PROBE FOR STACK GAS MONITORING SYSTEM

The present invention relates generally to industrial gas sampling systems and more particularly to an improved probe assembly for extracting gas samples from an industrial gas stream.

In U.S. Pat. No. 4,161,883 for "Conditioning Assembly for Continuous Stack Monitoring" by J. C. Laird et al. there is disclosed a probe assembly well suited to the extraction of gas samples from a gas stream which is heavily laden with particulate matter. The Laird et al. probe includes an inertial filter comprising a sintered metal porous sleeve through which a high velocity gas stream is induced to flow by an ejector. The porous sleeve is surrounded by a larger diameter cylinder from which gas samples are extracted for analysis. The extracted gas samples are free from particulates since solids entrained in the high velocity stream flowing axially through the filter sleeve possess high momentum and the sample gas is extracted orthogonally to the axial stream at a relatively low rate so as not to change significantly the momentum of the particles.

It has been found, however, that in certain installations involving stack gases of very high temperature and large concentrations of corrosive vapors, the Laird et al. type probe is subject to early failure. Both the filter sleeve and the ejector are attacked by the corrosives in the gases and the destruction of these elements is accelerated by the large volume of gases being handled and the high temperature of operation. Moreover, although clogging of the filter sleeve is minimized in the Laird et al. probe by prefiltering the stream and provision is made for cleaning the prefilter by periodic blowback, no provision is made for cleaning the filter sleeve by blowback. It is therefore necessary from time to time to disassemble the probe for cleaning of the filter sleeve.

It is an object of the present invention to provide a sampling probe assembly for an industrial gas monitoring system which is capable of withstanding continuous exposure to a high temperature, highly corrosive gas stream.

It is another object of the invention to provide a corrosion and temperature resistant stack gas sampling probe assembly which will supply particulate-free gas samples for analysis.

Still a further object of the invention is to provide a corrosion and temperature resistant stack gas sampling probe assembly which includes an inertial-type particulate filter with means for cleaning the same by periodic blowback.

Briefly, the invention comprises a stack gas sampling probe assembly combining inertial filter means with ejector-blowback valve means which generates a high velocity flow of stack gas through the filter and which provides means for periodically cleaning the filter of adherent matter by reversing the flow through the filter. The deleterious effects of corrosive gases and high temperature are eliminated by a probe assembly design which permits all parts exposed to the destructive gas stream to be formed of corrosion and temperature resistant ceramic material.

In the drawings:

FIG. 1 is an axial cross-sectional view of the probe of the invention;

FIG. 2 is a top view of the entry portion of the filter section of the probe;

Figure 3:
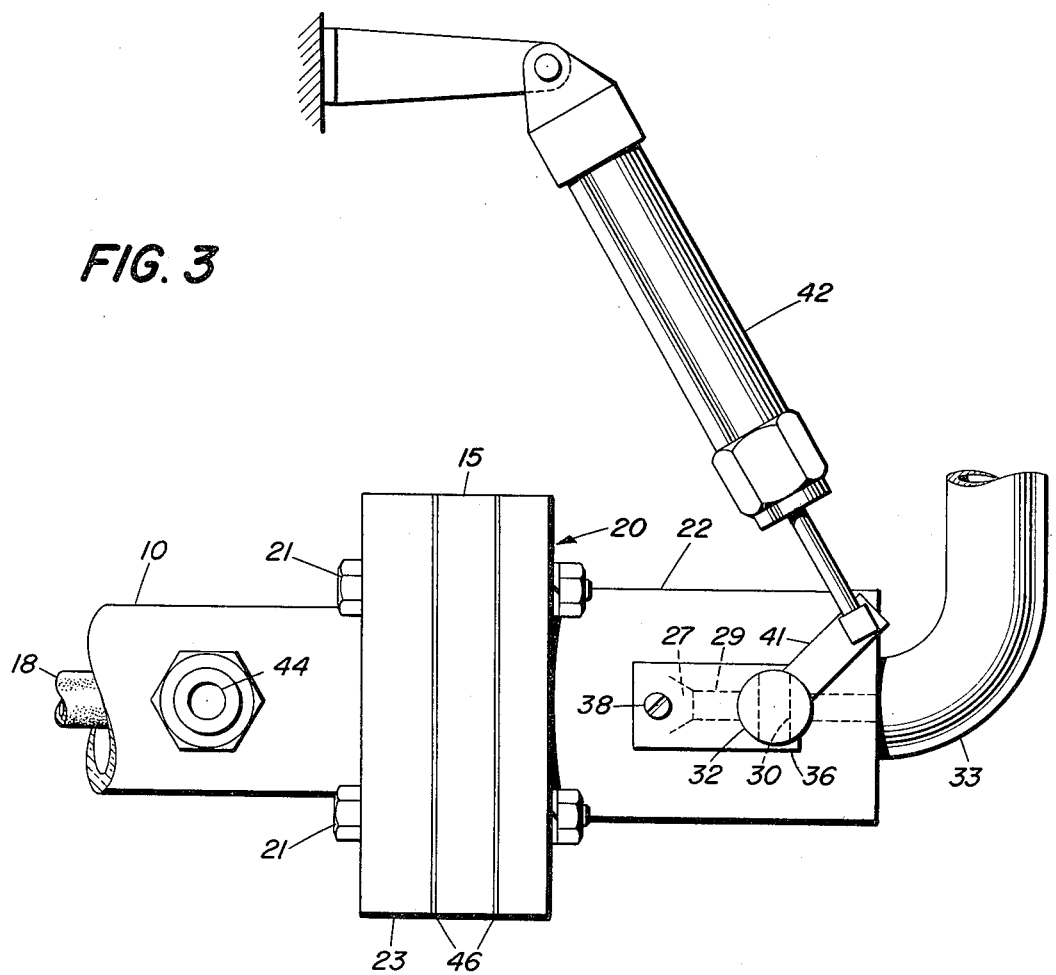
FIG. 3 is a top view of the combined ejector-blowback valve section of the probe.

Referring to FIG. 1, the probe of the invention comprises a ceramic tube 10 which is closed at the forward end by a ceramic plug 11 cemented therein. Tube 10 is secured to a mounting flange 12 which is formed of two semicircular disks clamped together by bolts 13 with tube 10 passing centrally therethrough. A gasket 14 surrounds tube 10 to provide a gas-tight, resilient seal with flange 12. Flange 12 is bolted in position at a breaching in a smoke stack so that the forward end of tube 10, bearing plug 11, projects into the stack stream. The rear end of tube 10, outside the stack wall, is closed by a flange-like ceramic plug 15 slidingly fitted therein. Both plugs 11 and 15 are provided with axial bores 16, 16'. The ends of bores 16, 16' facing the interior of tube 10 are counterbored to slidingly receive a cylinder 18 of porous ceramic material.

Tube 10 and cylinder 18 comprise an inertial filter. The outside diameter of cylinder 18 may suitably be about one-half the inside diameter of tube 10 thereby providing a space 19, closed at the ends by plugs 11 and 15, from which particulate-free gas samples may be withdrawn. A high velocity stream of stack gas, which may contain particulate matter, is induced to flow through bore 16, cylinder 18 and bore 16' by an ejector, later described, located downstream of bore 16'. Particles in the stack gas stream continue to move in the direction of the stream by virtue of their high momentum since the relatively small amount of gas from the stream diffusing into space 19 at a low rate does not significantly affect particle momenta.

Figure 4:
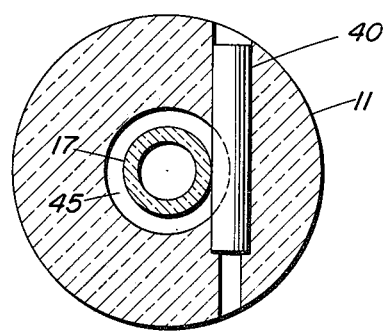
FIG. 4 is a sectional view taken along the line 4—4 of FIG. 1.

As seen in FIGS. 2 and 4, the probe may be extended farther into the stack stream by fitting a ceramic extension tube 17 into the nose of plug 11. The bore 16 of plug 11 is enlarged at the forward end for a sliding fit with tube 17. Tube 17 is secured to plug 11 by a pin 40 extending transversely through plug 11 to engage a circular slot 45 in the tube outer wall.

A combination ejector-blowback valve 20 is secured to the face of plug 15 by bolts 21 passed through the body 22 of ejector-valve 20, the flange portion of plug 15 and a backing plate 23 cemented to tube 10. Gaskets 46 provide gas tight seals between plug 15, body 22 and plate 23. The bolted assemblage of these parts provides convenient access to cylinder 18 for maintenance purposes.

Housing 22 contains a stepped cylindrical chamber 24 positioned coaxially with bore 16' of plug 15. An axially bored insert 26 having a base disk portion 25 integrally formed therewith is secured in coaxial alignment with bore 16' by engagement of the stepped portion 47 of chamber 24 with the insert base 25. The nose of insert 26 extends into a cavity 27 leading from chamber 24 with a circular clearance space 28 between the outer wall of insert nose and the wall of cavity 27. Cavity 27 converges toward and intersects a bore 29 of equal diameter and coaxial with bore 16'. A bore 31 of larger diameter than bore 29 extends transversely through body 22 to intersect bore 29.

A valve stem 32 having a bore 30 therein aligned with bore 29 is rotatably secured in body 22. Bore 29 leads to an exhaust tube 33 through which gases are returned to the stack. An inlet 34 in body 22 provides for the admission to chamber 24 of high pressure air or steam supplied through fitting 35. Body 22, insert 26 and valve stem 32 are each composed of ceramic material.

Referring to FIGS. 1 and 3, valve stem 32 is rotatably secured to body 22 by a metal fork 36, the tines of which engage a slot 37 in the upper portion of stem 32 and which is secured to body 22 by a screw 38 and compression spring 39. An arm 41 extending from valve stem 32 is coupled to a pneumatic actuator 42 for rotation of the valve between the open position shown in FIG. 1 and the closed position shown in FIG. 3. In the valve open position, pressure fluid from chamber 24 enters the convergent cavity 27 through clearance space 28 to set-up a high velocity flow through bore 29 which exits through exhaust tube 33. This flow induces a high velocity flow of stack gas through bore 16, cylinder 18 and bore 16' for discharge through exhaust tube 33. Substantially all particulate matter in the induced stack gas flow will be carried along with the flow and swept out though exhaust tube 33. During this period, particulate-free matter may be extracted for analysis from the space surrounding the exterior of cylinder 18 by pumping the sample from outlet 43 at a relatively low flow rate. A normally closed inlet 44 to the space surrounding cylinder 18 is provided for the purpose of admitting test gas when calibration of the analyzing apparatus connected to outlet 43 is required.

When valve stem 32 is rotated to the position of FIG. 3, bore 30 is rotated to a position transverse to bore 29 and bore 29 is blocked by the wall of stem 32. The back pressure in cavity 27 then rises substantially to the pressure of cavity 24 causing flow to be reversed through bore 16', cylinder 18 and bore 16. This reverse flow, or blowback, of clean fluid dislodges particulate matter which may be adhering to the inner wall of cylinder 18 and discharges the same through the forward end of the probe into the stack.

The ceramic materials found suitable for construction of the probe and ejector-blowback valve assembly comprise a material known to the trade as "Mullite", a composition of 60% silica and 40% alumina for tube 10, plug 11, plug 15 and tube 17. Body 22, insert 25 and valve stem 32 are formed of a material having a composition essentially of 99.5% aluminum oxide ($AL_2O_3$) available from Coors Porcelain Co., Golden, Colo. under catalog no. AD-995. Extension tube is formed of material comprising 99.8% aluminum oxide also available from Coors Porcelain Co. under catalog no. 30 AD-998. Cylinder 18 is formed of porous alumina silicate having a porosity of 10 microns or 100 microns, available from Coors Porcelain Co. under the designations P-10 and P-100, respectively. Plug 11, plate 23, outlet tube 43 and test gas inlet tube 44 are secured to tube 10 by cementing with an adhesive sold under the trade name "Ceramabond 503" by Aremco Products, Inc., Ossining, N.Y.

The invention claimed is:

1. A probe for the extraction of gas samples from a high temperature, particulate laden gas stream, comprising,
    an elongated tube;
    a pair of plugs having axial bores therein, said plugs being fitted in opposite ends of said tube with said bores in alignment;
    a hollow, porous walled cylinder supported by said plugs concentrically within said tube, said cylinder and said tube being dimensioned to provide a clearance space between the outer wall of said cylinder and the inner wall of said tube, said cylinder forming a conduit interconnecting said plug bores;
    means for admitting particle laden gas to be sampled to said bore of one of said plugs;
    means for withdrawing gas samples from said clearance space surrounding said porous cylinder;
    a combination ejector-blowback valve secured to the other of said plugs externally of said tube, said ejector-blowback valve including,
    a body, said body having therein
    a cylindrical chamber, a convergent walled cavity adjacent to and communicating with said chamber and an exit bore,
    said body being secured to said other plug with said chamber, said cavity and said exit bore coaxially aligned with said axial bore of said other plug,
    a hollow cylindrical insert supported in said body chamber coaxially with and forming an extension of said axial bore of said other plug, said insert extending the length of said chamber and into said cavity, said insert being dimensioned to provide a clearance space between the outer wall of said insert and the wall of said cavity;
    a transverse bore in said body intersecting said exit bore;
    a valve stem rotatably mounted in said transverse bore, said valve stem having a transverse aperture therein which is aligned with said exit bore in one rotational position of said stem, said exit bore being closed by said stem in a second rotational position of said stem; and
    means for admitting fluid under pressure to said body chamber; said tube, said plugs, said porous cylinder, said body, said insert and said valve stem each being formed of temperature 40 and corrosion resistant material.

2. A probe as claimed in claim 1 wherein said temperature and corrosion resistant material comprises a ceramic refractory material.

3. A probe as claimed in claim 2 wherein said means for admitting particle laden gas comprises,
    mounting means for securing said probe to a stack containing a flow of gases to be sampled, said probe extending through the wall of said stack with the end of said tube containing said one plug projecting into said flow of gases.

* * * * *